US011198863B2

United States Patent
Wang (10) Patent No.: US 11,198,863 B2
(45) Date of Patent: Dec. 14, 2021

(54) DISSECTION SYSTEM OF FORMALIN-FIXED PARAFFIN-EMBEDDED (FFPE) TISSUE SECTION FOR NUCLEIC ACID EXTRACTION

(71) Applicant: Dongfang Wang, Castro Valley, CA (US)

(72) Inventor: Dongfang Wang, Castro Valley, CA (US)

( * ) Notice: Subject to any disclaimer, the term of this patent is extended or adjusted under 35 U.S.C. 154(b) by 976 days.

(21) Appl. No.: 15/896,908

(22) Filed: Feb. 14, 2018

(65) Prior Publication Data

US 2018/0230454 A1 Aug. 16, 2018

Related U.S. Application Data (60) Provisional application No. 62/459,591, filed on Feb. 15, 2017.

(51) Int. Cl.
| | |
|---|---|
| *G01N 1/00* | (2006.01) |
| *C12N 15/10* | (2006.01) |
| *G01N 1/31* | (2006.01) |
| *B01L 3/00* | (2006.01) |
| *G01N 1/28* | (2006.01) |
| *G01N 1/36* | (2006.01) |

(52) U.S. Cl.
CPC .......... *C12N 15/1017* (2013.01); *B01L 3/508* (2013.01); *G01N 1/286* (2013.01); *G01N 1/31* (2013.01); *G01N 1/312* (2013.01); *G01N 1/36* (2013.01); *B01L 2200/085* (2013.01); *B01L 2200/087* (2013.01); *B01L 2300/0681* (2013.01); *B01L 2300/0832* (2013.01); *B01L 2400/0478* (2013.01); *G01N 2001/317* (2013.01)

(58) Field of Classification Search
None
See application file for complete search history.

(56) References Cited

U.S. PATENT DOCUMENTS 9,528,919 B2 * 12/2016 Fox .......................... G01N 1/44
2014/0099240 A1 * 4/2014 Misono ................. B01L 3/0217
422/514

OTHER PUBLICATIONS

Fassunke J. et al., Utility of different massive parallel sequencing platforms for mutation profiling in clinical sampls and identification of pitfalls using FFPE tissue. Int J Mol Med. 2015, 36(5):1233-1243.

(Continued)

*Primary Examiner* — Jyoti Nagpaul (57) ABSTRACT

A dissection system has a dissection platform which has a frame, an agitation platform, a tissue section tray, a solution dispenser unit, an airflow drying unit and a waste collection unit and a specimen collector which has a tubular body, a plunger button, a hollow shaft, a piston cylinder, a motor unit, a piston, a piston spring and a piston rod. The agitation platform, the solution dispenser unit, the airflow drying unit and the waste collection unit are disposed on the frame, and the tissue section tray is removably disposed on the agitation platform. The plunger button, the hollow shaft and the piston cylinder are movably inserted in the tubular body. The piston is slidably inserted within the piston cylinder, the piston spring is biased in between the piston cylinder and the motor unit, and the piston rod is connected in between the motor unit and the piston.

20 Claims, 7 Drawing Sheets

(56) References Cited

OTHER PUBLICATIONS

Sengüven B. et al, Comparison of Methods for the Extraction of DNA from Formalin-Fixed, Paraffin-Embedded Archival Tissues. Int J Med Sci. 2014, 11(5): 494-499.
Arreaza G, et al Pre-Analytical Considerations for Successful Next-Generation Sequencing (NGS): Challenges and Opportunities for Formalin-Fixed and Paraffin-Embedded Tumor Tissue (FFPE) Samples. Int. J. Mol. Sci. 2016, 17(9): 1579-1587.
Kocjan B.J. et al. Commercially available kits for manual and automatic extraction of nucleic acids from formalin-fixed, paraffin-ambedded (FFPE) tissues. Acta Dermatovenerol Alp Pannonica Adriat. 2015, 24(3):47-53.

\* cited by examiner

DISSECTION SYSTEM OF FORMALIN-FIXED PARAFFIN-EMBEDDED (FFPE) TISSUE SECTION FOR NUCLEIC ACID EXTRACTION

FIELD OF THE INVENTION

The invention relates to a method and a device system for dissection of targeted areas on Formalin-Fixed Paraffin-Embedded (FFPE) tissue sections mounted on glass slides. The targeted tissues are used for nucleic acid, DNA or RNA, extraction; the extracted nucleic acids are used for the application of genetic analyses in clinical medicine or bioscience research. Specifically, the invention aims to a novel technique and device system for picking microscopy-selected areas on FFPE tissue sections that can be about 2-4,000 $mm^2$ in size depending on the necessities such as the tissue types, the amount of nucleic acids required and the sizes of available tissue sections. The selected areas on FFPE tissue sections can be marked by related professionals using a microscope. The examples of the selected FFPE tissues are clinical physician interested-pathological changes in certain areas on human tissue sections, and biological scientist-interested certain areas on animal tissue sections. The advantage of selected picking certain area on tissue section instead of using whole tissue section is to minimize irrelevant molecules in the analyte thus to avoid false negative result of molecular assays. The invention is applicable in clinical molecular genetics analyses for the purpose of diagnosis, therapy, retrospective epidemiological studies and clinical research or other bioscience molecular biology studies in which FFPE tissue sections are used as specimens.

BACKGROUND OF THE INVENTION

The initiation of this invention is inspired by recent increased demand of the advancing molecular biology technologies and personalized medicine in that genetic targets become promising breakthrough points. As described by Fassunke J. et al: in the growing field of personalized medicine, the increasing number of molecular targets for individualized therapies requires the analysis of numerous, potential genetic alterations, which is becoming a challenge in terms of workload, tissue availability, as well as costs (1). Extraction of nucleic acids from fresh tissues should be more suitable for genetic analyses in terms of the quality of nucleic acids; however the major limitation in clinical setting using fresh tissue is the availability on time particularly collecting the inner organ tissues from patients. In many cases the available tissues are archived FFPE tissue sections obtained from previous biopsy or surgery. FFPE tissue has the advantage of being stored at room temperature for decades and allowing the nucleic acids to be recovered and analyzed. Many approaches to extract DNA from FFPE tissues for use in molecular analyses, such as polymerase chain reaction (PCR), real-time quantitative PCR, single nucleotide polymorphism (SNP) analyses and whole genome sequencing, have been reported (2). FFPE is likely to be the preferred choice for tissue preservation in clinical practice for the foreseeable future. Multiple analyses are routinely performed on the same FFPE samples (such as immunohistochemistry, in situ hybridization, RNAseq, DNAseq, TILseq, Methyl-Seq, etc), thus, specimen prioritization and optimization of the isolation of analytes are critical to ensure successful completion of each assay (3).

Nucleic acids extraction from FFPE tissue is a multistep process, the pre-extraction dissection including FFPE tissue deparaffinization and dissection is critical for the quality and yield of the extracted nucleic acids. There are many commercial reagent kits are available (4) for FFPE tissue nucleic acids extraction; however for selectively picking targeted and small tissue on slides, particularly fine needle biopsies that can be as small as a few $mm^2$ in size, manual FFPE tissue specimen dissection is still the conventional approach currently in biomedical laboratories. Manual FFPE tissue specimen dissection is a multiple-step procedure including several rounds of deparaffinization solution treatment in staining jars with frequent flipping, tissue section air drying, adding nucleic acid extraction solution on FFPE tissue sections, scraping tissue using sterile scalpel and collecting specimen by a pipette. In summary, there are four steps in manual FFPE tissue dissection: tissue deparaffinization and drying, tissue softening treatment, scalp scraping, and collection of dissected tissue mix solution by pipetting. Those manual operation steps are time consuming, labor intensive and ergonomic unfriendly due to the need of intensive finger and wrist movements, particularly when medium or larger number of specimens need to be processed routinely; in addition, a risk of tissue cross contamination exists when multiple tissue section slides are placed in a staining jar for deparaffinization. Another option for dissection of small FFPE tissue on slide is the laser micro-dissection. Laser micro-dissection is able to pick up micro-size tissue precisely, but the application is much more costly and even more time consuming in comparison with conventional manual dissection. There are several commercially available "automated FFPE tissue systems" for nucleic acids extraction (4), however, FFPE tissue specimen dissection prior extraction is not a part of the automation, and tissue cut form FFPE tissue blocks without mounting on slide is not further selectable for particular areas in the tissue to meet specific needs, thus the above mentioned manual FFPE tissue dissection method remains to be the most common used technique in biomedical laboratories. A new developed AVENIO Millisect System offered by Roche Diagnostics is available on market; it is an automated digitally-assisted alignment and dissection system that selectively isolates FFPE tissue areas by a rotary blade. However FFPE tissue deparaffinization is not a part of the automation, and only four slides can be placed on its work station, in addition the operation cost is a concern due to the sophisticated instrument.

It is apparent that a need exists for a FFPE tissue dissection system which remains the benefits of manual dissection method, that is target area selective and small tissue collectable, but avoids the mentioned drawbacks; in other words, to obtain better working efficiency and lower cost, and to minimize hand stress injury risk. These are this invention's objectives. This invention integrates all the said FFPE tissue dissection steps by a system including a dissection platform of FFPE tissue sections and an electric specimen collector. The system markedly improves work efficiency and labor cost, and reduces ergonomic burden in comparison with conventional manual method; in addition it avoids the risk of tissue cross contamination during deparaffinization. It is a highly valuable option for medium throughput FFPE tissue dissection process. The device system itself is simple, easy to use and inexpensive to manufacture.

SUMMARY OF VARIOUS EMBODIMENTS OF THE INVENTION

The invention centers on a novel concept of providing an efficient, inexpensive and ergonomic method and a device system for dissection of target FFPE tissues for nucleic acids extraction in biomedical science applications. The invention includes two devices: one is a dissection platform for FFPE tissue deparaffinization, the device is termed as "dissection platform" below; and the second device is a specimen collector for liquid pipetting, tissue scraping and collecting.

The said dissection platform allows ten or more FFPE tissue section slides to be placed and processed each batch. A tissue section tray is placed on the top of this dissection platform and is removable; when one batch of the tissue sections is completed in dissection, the tissue section tray can be removed and a new tray with the second batch of sections is replaced on the dissection platform. In general, based on this inventor's experience, nucleic acids extracted from 10 mm$^2$ of a 10-mm thick tissue section is suitable for multiple setups of a PCR or DNA sequencing based test. Deparaffinization solution, xylene or other commercial available deparaffinization solution is added into the tissue section tray, high frequent agitation, generated by a vibration motor which is mounted underneath an agitation platform, facilitates FFPE tissue deparaffinization during deparaffinization solution incubation. Deparaffinization solution is drained down to a waste collection unit after deparaffinization by a vacuum pump, and then sections are dried by an airflow drying unit.

FFPE tissue nucleic acid extraction solution (simplified as the term "extraction solution" below), which can be in-house made or commercial reagent, is added on and it covers the targeted tissue areas marked by related professionals using the said specimen collector attached with a specific designed specimen tip. The suitable incubation time ranges from 1-3 minutes to soften FFPE tissue depending on the tissue types. The second function of the specimen collector is to scrape or rub the extraction solution softened tissue on slide by a motor-driven and slow spinning specimen tip which is the same tip used for liquid pipetting; the spinning tip detaches tissue from the slide. The scraped tissue with the extraction solution is then drawn into the same specimen tip and dispensed into a collection micro-tube on the dissection platform.

The various embodiments in this invention may include variations in the shape, size, material of all parts, type of electric mini fan, vibration motor and specimen collector motor, may also include construction method of the device frame, tissue section tray, agitation platform and piston assembly of the specimen collector.

BRIEF DESCRIPTION OF THE DRAWINGS

The drawings, which are simplified and are not necessarily drawn to scale, illustrate the method and device system of this invention, although it will be understood that such drawings depict preferred embodiments of the invention and, therefore, are not to be considered as limiting its scope with regard to other embodiments which the invention is capable of contemplating.

FIG. 1 is an illustration showing a top-view diagram of the dissection platform. The dissection platform basically includes a frame, a removable tissue section tray for accommodating FFPE sections, an agitation platform with a vibration motor mounted underneath the agitation platform, and a mini fan driven airflow drying unit for removing deparaffinization solution residue after used solution is drained down to a waste collection unit. There is a deparaffinization solution dispenser unit for dispensing deparaffinization solution from a container into tissue section tray.

FIG. 3A shows the dissection platform without tissue section tray, thus the agitation platform is visible. There is a vibration motor mounted on the bottom side of the agitation platform, the motor generates high frequency vibration and causes agitation of deparaffinization solution in the tissue section tray to maximize the solution's effect. FIG. 3A also illustrates an airflow drying unit which is used to dry the tissue sections completely after deparaffinization is completed. FIG. 3B shows an upper perspective view of the detached tissue section tray. FIG. 3C illustrates the bottom side of the tissue section tray where there is a rectangle block for holding with agitation platform. There is a rectangle indent in the agitation platform, matching the size of the said rectangle block on tissue section tray in order to hold tissue tray together while agitation occurs.

FIG. 4A illustrates a back view diagram of the dissection platform. The air duct and two min fans of the said airflow drying unit, deparaffinization solution dispenser unit including a dispenser and a dispenser guarding rail, and the agitation platform with a vibration motor are shown. FIG. 4B is a side view diagram of the dissection platform. The top of the airflow drying unit and deparaffinization solution dispenser unit are shown. The agitation platform, mini fans and vacuum pump are shown by dot line drawing. The said dispenser can be manual operated by moving it to a desired position and pushing a piston device or squeezing a soft solution container for liquid dispensing; or the said dispenser can be automatically operated by a stepper motor, a liquid pump and an electronic controller to move the dispenser on dispenser guarding rail and dispense desired amount of solution into the tissue section cells, the details of the dispenser unit are not shown.

FIG. 5 is a side view diagram illustrating the said specimen collector. The specimen collector functions as both a liquid pipette and a tissue section scrapper. Using the specimen collector, the extraction solution is added on tissue section incubating the tissue for 1 to 3 minutes depending on the tissue type and the formula of the extraction solution. When the specimen collector is used for tissue section scrapping, a motor rotates the whole piston assembly cylinder along with a specimen tip connected. The end of spinning specimen tip is placed on selected area of the tissue section to scrap the tissue off glass slide; finally the specimen collector draws scraped tissue debris that mixed with extraction solution and transfers the mixture into a collection tube.

FIG. 6 is a cross sectional view diagram illustrating the specimen collector. For liquid pipetting, the movement a piston assembly is controlled by a spring which is between the piston assembly cylinder and a slow-speed motor. A plunger button directly contacts the motor, when the plunger button is pushed, the piston expels air out of the piston cylinder; when the plunger button is released, the compressed spring pushes the piston assembly back to standby position and draws extraction solution into the specimen tip; when the plunger button is pushed again, the solution is added on tissue. For tissue dissection, the motor is switched on, it drives a specimen tip which is attached on the low end of the said specimen collector to spin and scrape or rub FFPE tissue section. After the FFPE tissue specimen is detached from slide, the tissue extraction solution with detached tissue specimen is drawn back to the specimen tip, and then expelled into a specimen collection tube.

FIG. 7 illustrates two types of specimen tips for the specimen collector. One is a wider tip for large tissue section; the other is a thinner needle tip for small tissue section. The ends of the tips are flat and coated with a coating layer made of, for instance, a rubber material, however the material used for the tip end coating layer is not limited to rubber. Materials with similar degrees of firmness are within the scope of this dissection application, such as plastics or polymers. The tip end is designed for better tip-tissue section contact; the tips are one time use and disposable.

DETAILED DESCRIPTION OF THE INVENTION

Figure 1:
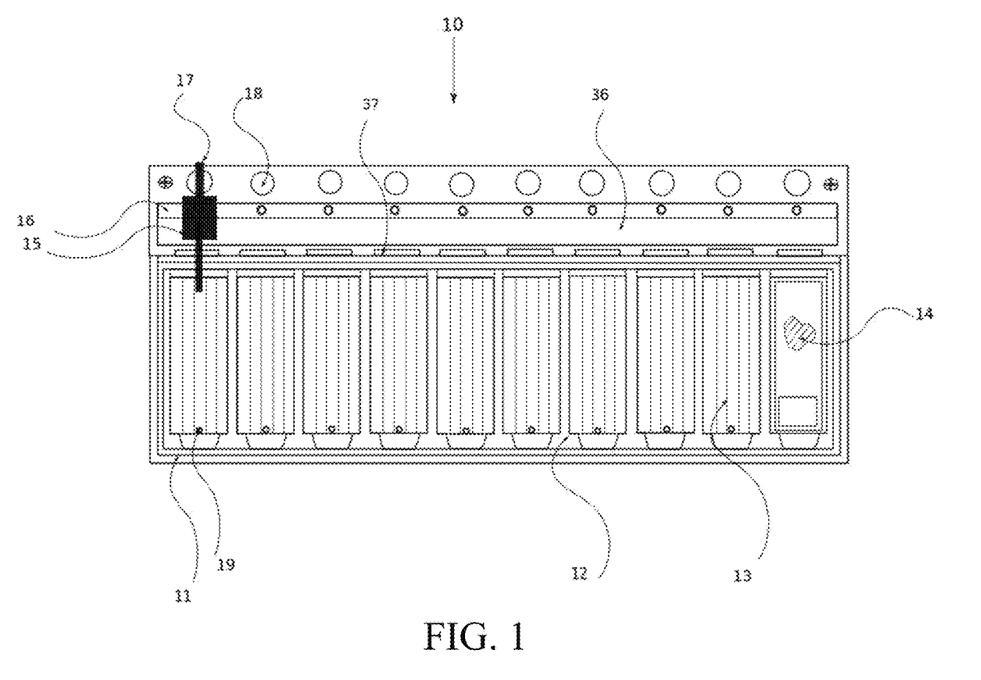

The dissection system of FFPE tissue section for nucleic acid extraction includes two devices: a dissection platform 10 for FFPE tissue section deparaffinization and a specimen collector 40 for liquid pipetting and tissue scrapping. Referring to FIG. 1 though FIG. 4B, the drawings show simplified diagrams of the dissection platform 10; referring to FIG. 5 though FIG. 7, the drawings show simplified diagrams of the specimen collector 40. The figures, which are simplified and are not necessarily drawn to scale, illustrate the method and device system of this invention, although it will be understood that such drawings depict preferred embodiments of the invention and, therefore, are not to be considered as limiting its scope with regard to other embodiments which the invention is capable of contemplating.

A. The Dissection Platform

Referring to the dissection platform 10, it is mainly comprised of a frame 11, a removable FFPE tissue section tray 12, a deparaffinization solution dispenser unit 15, 16, 17 an agitation platform 20, a waste collection unit 19, 31, 32, 33, 34 and an airflow drying unit 35, 36, 37, 38.

FIG. 1 is a top-view diagram of the dissection platform 10. The dissection platform is used for FFPE tissue deparaffinization when a tissue section tray 12 is placed on. The tissue section tray 12 is for accommodating FFPE tissue sections 14 mounted on glass slides and deparaffinization solution. The tissue section tray 12 in this diagram has ten rectangle tissue section cells 13, but the number of cells 13 with regard to this invention is not limited as shown in the diagram Each cell is for one FFPE tissue section 14, and separated from each other in order to prevent tissue sample cross contamination during the treatment of deparaffinization solution in case there is peeling-off of tissue debris. The front and rear ends of each cell 13 are inward-slanted, and the bottom is ridge shaped allowing airflow to pass by under the glass slides of tissue sections 14 for drying the bottom side of the glass slides after deparaffinization. Deparaffinization solution is dispensed into the tissue section cells 13 covering FFPE tissue sections 14. The tissue section tray 12 in this figure is designed for one tissue section 14 from a particular FFPE tissue sample per cell 13, for example, a section of a patient's neck skin biopsy. When multiple tissue sections cutting from a same FFPE tissue block are required, meaning larger amount of nucleic acid is needed or the tissue sections 14 are too small, multiple tissue section cells 13 are used for the same source tissue sections 14. In general, based on the inventor's experience, if the size of a tissue section 14 is 10-mm thick and larger than 10 mm$^2$, the amount of nucleic acid extracted is enough for multiple PCR or sequencing test set-ups. A deparaffinization solution dispenser unit which includes a solution dispenser 15 and a dispenser guarding rail 16 are shown; the intake end 17 of this dispenser 15 is connected to a deparaffinization solution container (not shown). The said dispenser 15 can be manual operated by moving to desired positions and pushing a piston device or squeezing a soft solution container for liquid dispensing; or the dispenser 15 can be automatically operated by a stepper motor, a liquid pump and an electronic controller to move on the dispenser rail 16 and dispenses desired amount of solution into the tissue section cells 13. The said piston device, solution container, stepper motor, electric controller and the pump of the dispenser are not shown.

As shown in FIG. 1 there are ten micro tube holes 18 at the back of the dissection platform 10; each tube hole 18 aligns a tissue section cell 13. The tube holes 18 are designed for holding 1.5 ml micro tubes for dissected tissue specimens.

Figure 2:
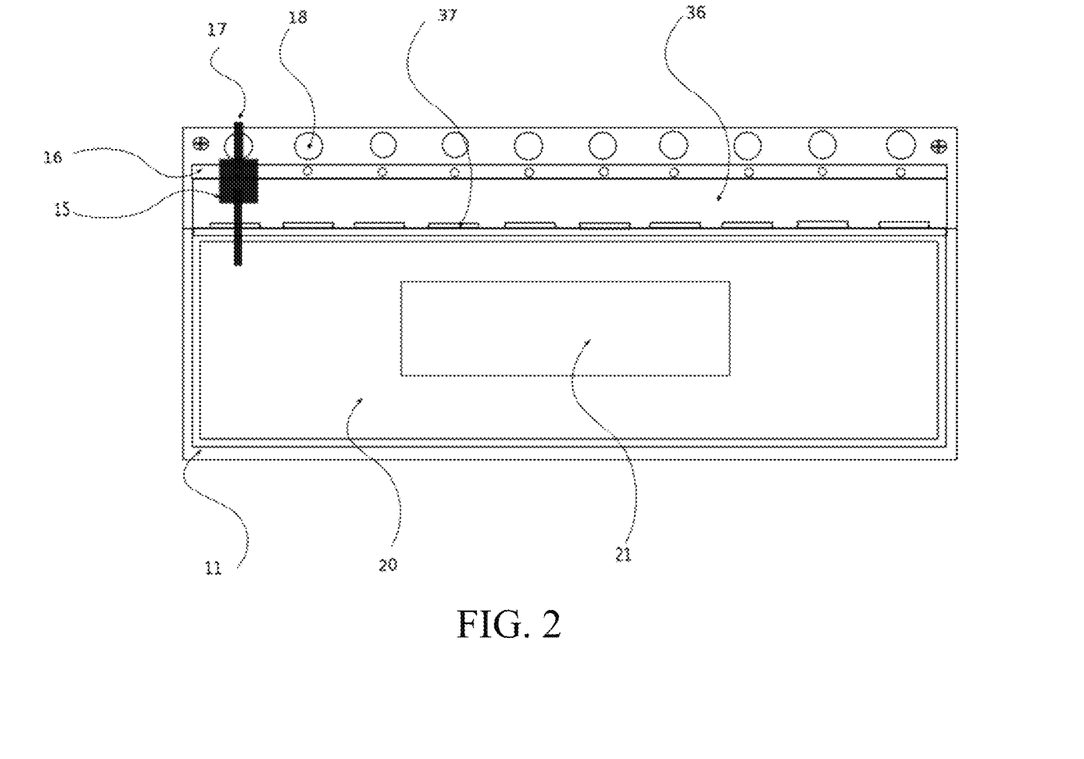
FIG. 2 is an illustration showing a top-view diagram of the dissection platform without the said tissue section tray. The tissue section tray is removed from the agitation platform after completion of tissue dissection for cleaning. A new tray can be replaced on the agitation platform for second batch FFPE tissue sections.

FIG. 2 illustrates a top-view diagram of the dissection platform 10 when tissue section tray 12 is removed. The tissue section tray 12 is removed from the agitation platform 20 after completion of tissue dissection for cleaning; a clean tissue section tray 12 can be replaced on the agitation platform 20 for second batch tissue sections 14. There is a rectangle indent 21 in the agitation platform 20 for holding tissue section tray 12 in place while agitation occurs, accordingly there is a rectangle block 22 (as shown in FIG. 3C) on the bottom side of the tissue section tray 12 matching the size of the said rectangle indent 21 in the agitation platform 20.

Figure 3A:
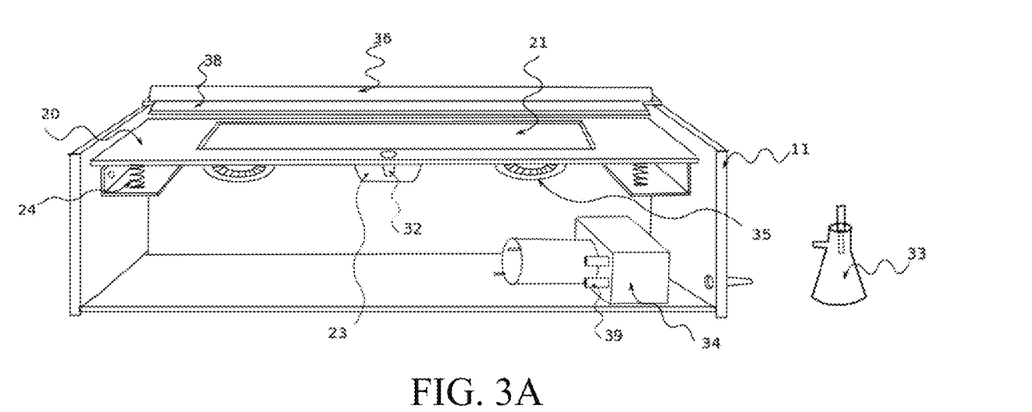
FIG. 3A, FIG. 3B and FIG. 3C are illustrations demonstrating that the said tissue section tray is removed from the dissection platform.
Figure 3B:
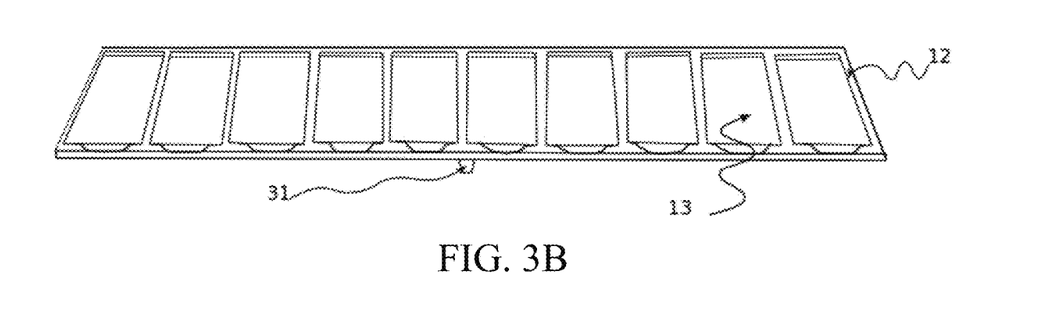
Figure 3C:
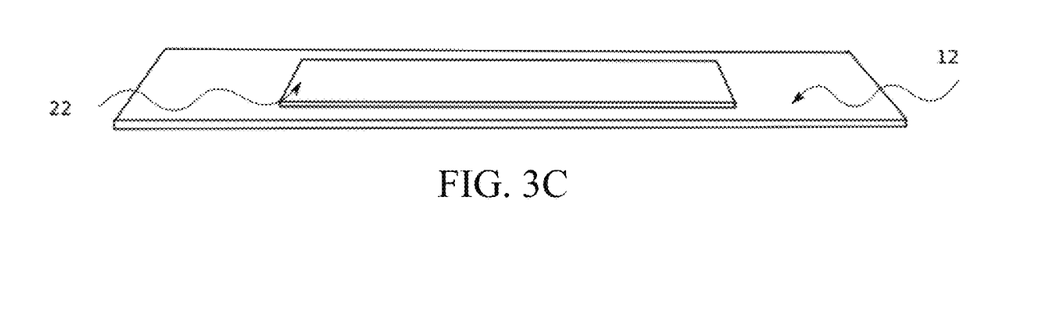

FIG. 3A, FIG. 3B and FIG. 3C show that the tissue section tray 12 (FIG. 3B) is removed from the agitation platform 20. FIG. 3A illustrates the dissection platform 10 without tissue section tray 12, thus the agitation platform 20 is visible. There is a rectangle indent 21 in the agitation platform 20 for holding tissue section tray 12 in place with agitation platform while agitation occurs; accordingly there is a rectangle block 22 on the bottom side of the tissue section tray 12 (FIG. 3C) matching the size and shape of the said rectangle indent 21 in the agitation platform 20. A vibration motor 23 is mounted on the bottom side of the agitation platform 20. In this current prototype of the dissection platform 10, the vibration motor 23 is 9V DC powered, spins at 3,100 rpm and causes agitation of the agitation platform 20. However, functionally comparable motors may be used instead of the said motor 23 in the prototype. There are four springs 24; each is attached at a corner of the bottom side of the agitation platform 20. The springs 24 support the agitation platform 20 and facilitate agitation of the agitation platform 20. High frequent agitation of deparaffinization solution results in a better reaction between deparaffinization solution and FFPE tissue. One round of deparaffinization with 3 minutes agitation is able to remove paraffin completely in comprising with the staining jar method that multiple rounds of deparaffinization are needed with frequent flipping.

A waste collection unit of the dissection platform 10 for discarding used deparaffinization solution is illustrated in FIG. 1, FIG. 3A, FIG. 3B and FIG. 3C. As shown in FIG. 1, there is a waste draining hole 19 in each of the FFPE tissue section cells 13. The waste draining holes 19 are connected to a waste outlet 31 (FIG. 3B) on the bottom of the tissue section tray 12. When the tissue section tray 12 is placed on agitation platform 20, the waste outlet 31 is inserted into an adaptor 32 on the agitation platform 20, the adaptor 32 is then inserted into a hose (not shown) that connects to a vacuum flask 33. When a vacuum pump 34 is switched on, it sucks air out of vacuum flask 33 via another hose (not shown) between vacuum pump air intake 39 and vacuum flask 33; the deparaffinization solution waste is then drained down from tissue section cells into the said vacuum flask 33. There is a tissue section airflow drying unit which includes two mini fans 35 and an air duct 36. The two mini fans 35 connect to the air duct 36 and drive air out of it though air outlet slots 37 (FIG. 1, FIG. 2). Each air outlet slot 37 faces a corresponding tissue section cell 13 in which a FFPE section 14 is deparaffinized. In the current prototype of the dissection platform 10, the mini fans 35 are 9V DC powered, however, functionally comparable min fans can be used in the application scope instead of the said min fans 35 in the prototype. An air damper 38 is attached up to the air outlet slots 37 to facilitate airflow moving forward.

Figure 4A:
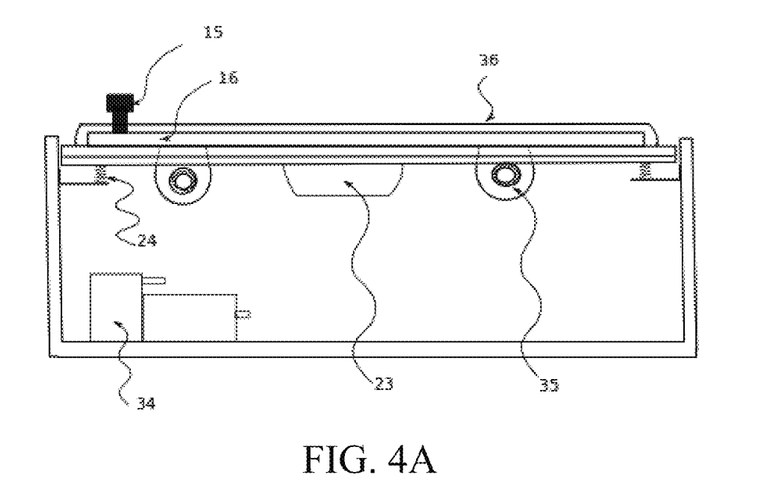
Figure 4B:
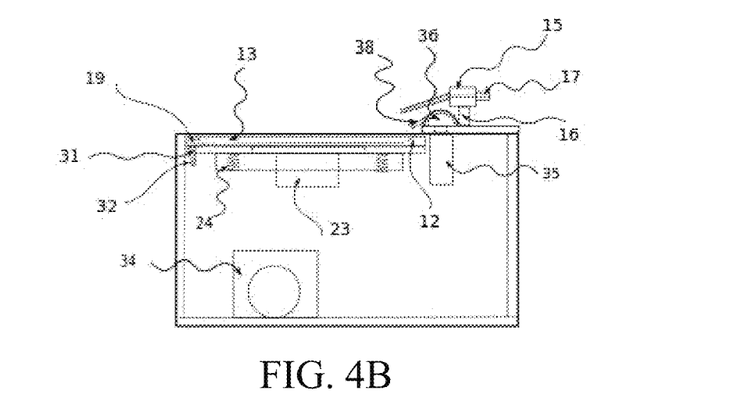

FIG. 4A illustrates a back-view diagram of the dissection platform 10. The airflow drying unit is shown, which includes two min fans 35 that connect an air duct 36. The vibration motor 23 mounted on the agitation platform 20, vacuum pump 34 for waste collection, deparaffinization solution dispenser 15 and dispenser guarding rail 16 are shown. FIG. 4B illustrates a side-view diagram of the dissection platform 10. Agitation platform 20, mini fan 35 and vacuum pump 34 are illustrated by dot lines. Tissue section cell 13 of the FFPE tissue section tray 12, waste draining hole 19 in the tissue section cells 13 and waste outlet 31 of the tissue section tray 12 are also shown by dot lines.

B. FFPE Tissue Specimen Collector

Figure 5:
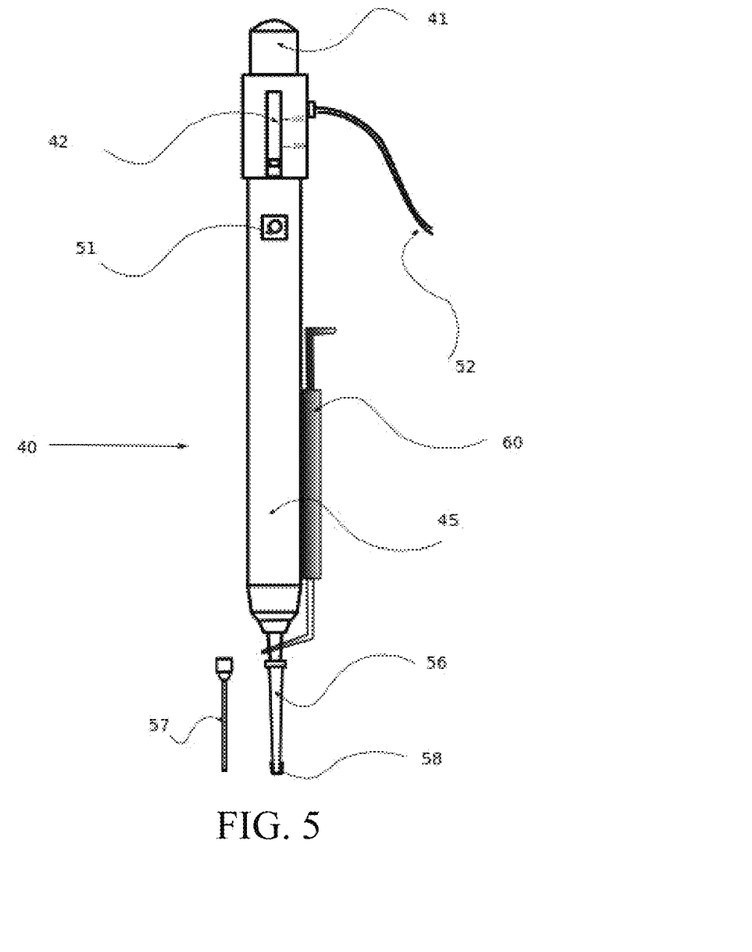

FIG. 5 is a side view diagram illustrating the specimen collector 40. The specimen collector 40 functions as both a liquid pipette for FFPE tissue extraction solution and a FFPE tissue section scraper. The volume of FFPE tissue extraction solution required for one FFPE tissue section is usually 25 to 150 µl depending on the sizes of the tissue sections. The volume can be measured when manually push down the plunger button 41 and view volume labels on a side-window 42 of the specimen collector body 45 ranging between 10 to 200 µl. Operator pushes and releases the plunger button 41 slowly to draw desired volume of the said extraction solution from a container, the extraction solution can be in-house made or commercial reagents. Operator then pushes the plunger button 41 all the way down to dispense the extraction solution on a targeted area of a FFPE tissue section 14. The FFPE tissue is incubated with the extraction solution for 2 to 5 minutes depending on the efficacy of the extraction solution used. When motor 43 (FIG. 6) is turned on by pushing a switch button 51, it drives the whole piston assembly cylinder 50 (FIG. 6) along with a hollow shaft 44 (FIG. 6) and a specimen tip 56 or 57 to scrape or rub the tissue section. The specimen collector 40 is adapted for attachment of two types of disposable specimen tips, one is a wider tip 56 for large section specimen collection, the other is thinner needle tip 57 for small needle biopsies sections. The details of specimen tips 56, 57 are shown in FIG. 7. The specimen tips 56, 57 are single tissue section use. A tip ejector assembly 60 is used for detaching used specimen tip 56 or 57. The motor 43 can be powered by an external power supply 52 or an internal rechargeable battery (not shown).

Figure 6:
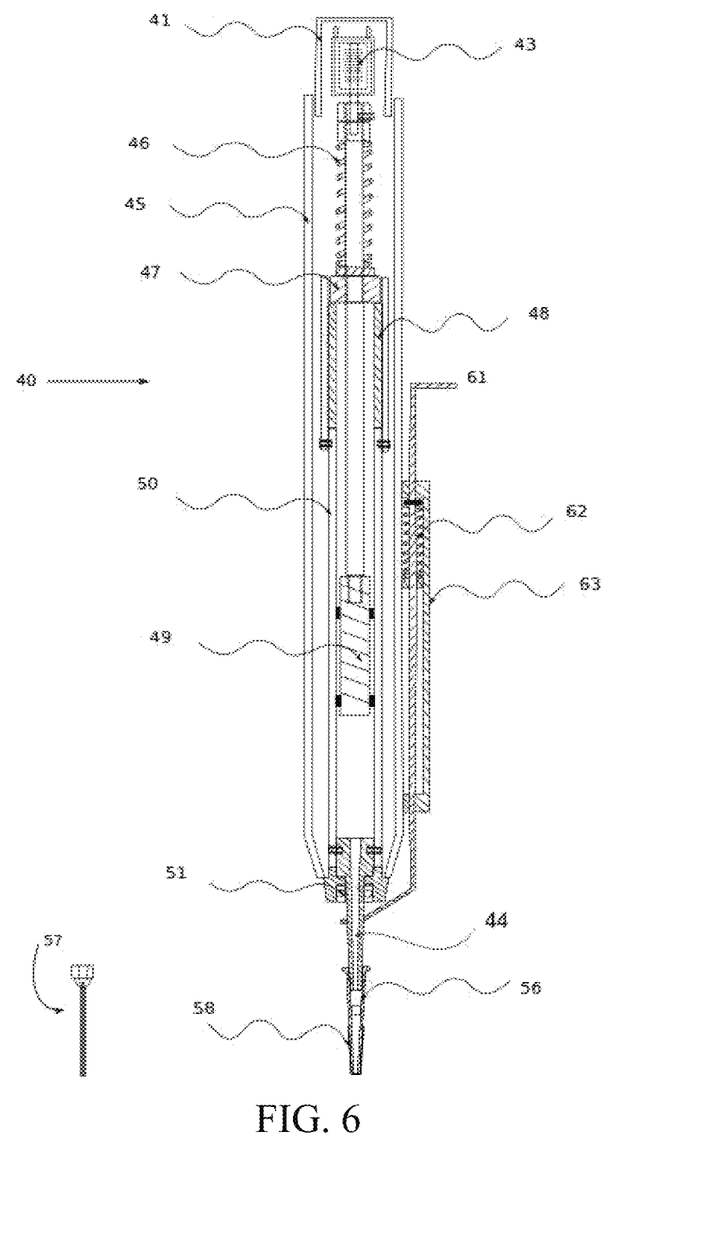
Figure 7:
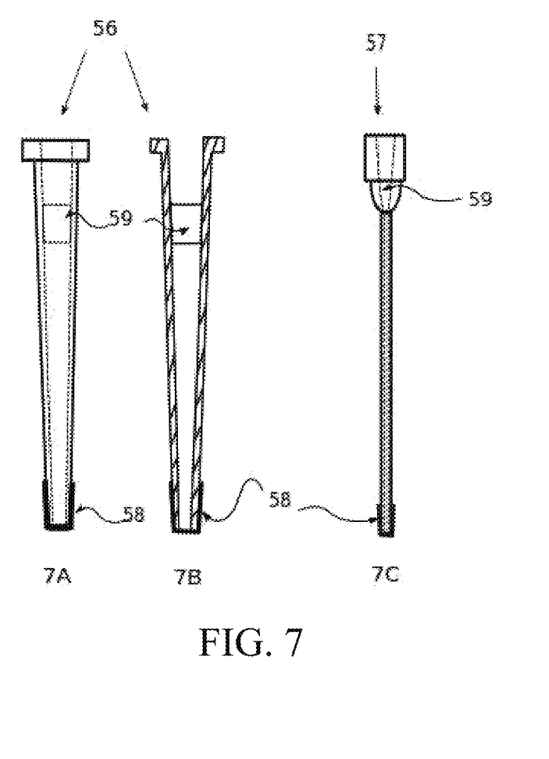

FIG. 6 is a cross sectional view diagram illustrating the specimen collector 40. The hollow shaft 44 attaches a specimen tip 56 or 57, and its top end connects a piston assembly cylinder 50. The specimen collector 40 draws or dispenses air or liquid when the piston assembly 49 moves up or down. The piston assembly 49 is controlled by a spring 46 between the piston assembly cylinder 50 and a slow speed motor 43. A plunger button 41 directly contacts the motor 43. When the plunger button 41 is pushed down, the piston assembly 49 expels air out of the piston cylinder 50 through the hollow shaft 44; when the plunger button 41 is released, the compressed spring 46 between plunger button 41 and piston assembly 49 pushes the piston assembly 49 back to standby position and draws liquid into the specimen tip 56 or 57 which is attached to the hollow shaft 44 and when the tip end is placed in liquid. There is a position retainer 47 under the spring 46, this retainer 47 is able to move up or down with piston assembly 49 when the plunger button 41 is moving up or down, but cannot turn if the motor 43 is off, because the two side-pins of the retainer 47 are allowed to move up and down within two grooves 48 in the inner wall of the piston assembly cylinder 50. When motor 43 is turned on, the two side-pins of the retainer 47 drive the entire piston cylinder 50 along with the hollow shaft 44 to spin. In the current prototype, the motor 43 is 9V DC powered, spinning at 300 rpm; however other motors with comparable functions can be used in the application scope of this invention. A bearing 51 is placed on the hollow shaft 44 to facilitate the spinning of the hollow shaft 44 along with specimen tip 56 or 57. The end of tip 56 or 57 is then able to scrape or rub the FFPE tissue section 14 which is covered with extraction solution. After the targeted FFPE tissue is detached by scraping or rubbing, the extraction solution with tissue specimen is drawn back by the same tip 56 or 57 and dispensed into a micro tube placed in a tube hole 17 in the dissection platform 10. A tip ejector assembly 60 including an ejection arm 61, an ejection spring 62 and a housing 63 is for detaching used specimen tip 56 or 57.

FIG. 7 illustrates two types of specimen tips for the specimen collector 40. One is a wider tip 56 for large sections as shown in 7A and 7B, they are simplified side and cross sectional view diagrams respectively; the other is a thinner needle tip 57 as shown in a side view diagram 7C. The end of the tip 56 or 57 is flat and coated with a coating layer 58, specifically, a rubber layer 58, however the material used for the tip end coating layer 58 is not limited to rubber. Materials with similar degrees of firmness are within the scope of this dissection application, such as plastics or polymers. Rubber tipped end is designed for better tip-tissue section contact, thus the tips are able to contact and scrape or rub tissue sections better. The thinner tips 57 are suitable for small sections such as needle biopsy sections or when small volume extraction solution (10-25 µl) is required. In addition, the thinner tips 57 are able to select small spots on tissue sections to avoid contacting nearby tissue. There is a filter 59 in the tip 56 or 57 for avoiding contamination of the specimen collector 40.

What is claimed is:
1. A dissection system comprising:
a dissection platform;
a specimen collector;
the dissection platform and the specimen collector being operatively associated with each other;
the dissection platform comprising a frame, an agitation platform, a tissue section tray, a solution dispenser unit, an airflow drying unit and a waste collection unit;
the agitation platform being movably connected with the frame;
the tissue section tray being removably connected with the agitation platform;
the solution dispenser unit being disposed on the frame;
the airflow drying unit being disposed on the frame;
the waste collection unit being disposed on the frame;

the specimen collector comprising a tubular body, a plunger button, a hollow shaft, a piston cylinder, a motor unit, a piston, a piston spring and a piston rod;
the hollow shaft and the piston cylinder being connected with each other;
the motor unit being configured to rotate the hollow shaft and the piston cylinder;
the motor unit being accommodated within the plunger button;
the motor unit contacting against the plunger button;
the piston being slidably inserted within the piston cylinder;
the piston spring being biased in between the piston cylinder and the motor unit; and
the piston rod being connected in between the motor unit and the piston.

2. The dissection system as claimed in claim 1 comprising:
the agitation platform being maintained in a horizontal position with respect to the frame.

3. The dissection system as claimed in claim 1 comprising:
the agitation platform comprising an indent;
the tissue section tray comprising a block; and
the tissue section tray being connected with the agitation platform by the indent and the block being engaged with each other.

4. The dissection system as claimed in claim 1 comprising:
the frame comprising a plurality of tube holes;
the tissue section tray comprising a plurality of tissue section cells;
the plurality of tube holes being separate from each other;
the plurality of tissue section cells being separate from each other;
a bottom of each of the plurality of tissue section cells being of ridge shaped; and
a corresponding tube hole among the plurality of tube holes being aligned with a corresponding tissue section cell among the plurality of tissue section cells in response to the agitation platform being connected with the frame and the tissue section tray being connected with the agitation platform.

5. The dissection system as claimed in claim 1 comprising:
the tissue section tray comprising a plurality of tissue section cells;
the airflow drying unit comprising a fan, an air duct and a plurality of air outlet slots;
the fan, the air duct and the plurality of air outlet slots being in fluid connection with one another;
a corresponding air outlet slot among the plurality of air outlet slots facing towards a corresponding tissue section cell among the plurality of tissue section cells in response to the agitation platform being connected with the frame and the tissue section tray being connected with the agitation platform;
the dissection platform comprising a switch unit;
the switch unit being disposed on the frame; and
the fan being electrically connected with the switch unit.

6. The dissection system as claimed in claim 1 comprising:
the tissue section tray comprising a plurality of tissue section cells;
the tissue section tray comprising a third waste outlet;
the waste collection unit comprising a vacuum flask and a vacuum pump; and
the vacuum flask and the vacuum pump being configured to be in fluid connection with one another.

7. The dissection system as claimed in claim 1 comprising:
the specimen collector comprising a side window and a label;
the side window being formed on the tubular body;
the label being disposed on the plunger button; and
the label being exposed via the side window.

8. The dissection system as claimed in claim 1 comprising:
the specimen collector comprising a pin;
the pin being connected with the piston rod;
the piston cylinder comprising an inner wall and a groove;
the groove being formed on the inner wall; and
the pin being slidably inserted into the groove.

9. The dissection system as claimed in claim 1 comprising:
the specimen collector comprising a bearing; and
the bearing being connected in between the hollow shaft and the piston cylinder.

10. The dissection system as claimed in claim 1 comprising:
the specimen collector comprising a hollow tip;
the hollow tip being connected with the hollow shaft; and
the hollow shaft being connected in between the piston cylinder and the hollow tip.

11. The dissection system as claimed in claim 10 comprising:
the specimen collector comprising a filter;
the filter being accommodated within the hollow tip;
the hollow tip comprising an intermediate section, a flat end and a coating layer;
the intermediate section being of a conical shaped or a cylindrical shaped; and
the coating layer being coated on the flat end.

12. The dissection system as claimed in claim 10 comprising:
the specimen collector comprising a tip ejector;
the tip ejector being disposed on the tubular body and the hollow tip;
the tip ejector being configured to detach the hollow tip;
the tip ejector comprising an arm, a housing and an ejection spring;
the housing being fixed on the tubular body;
the arm being slidably disposed on the tubular body and the hollow tip;
the ejection spring being biased in between the arm and the housing.

13. A dissection system comprising:
a dissection platform;
a specimen collector;
the dissection platform and the specimen collector being operatively associated with each other;
the dissection platform comprising a frame, an agitation platform, a tissue section tray, a solution dispenser unit, an airflow drying unit and a waste collection unit;
the agitation platform being movably connected with the frame;
the tissue section tray being removably connected with the agitation platform;
the solution dispenser unit being disposed on the frame;
the airflow drying unit being disposed on the frame;
the waste collection unit being disposed on the frame;
the agitation platform being maintained in a horizontal position with respect to the frame;
the agitation platform comprising an indent;

the tissue section tray comprising a block;
the tissue section tray being connected with the agitation platform by the indent and the block being engaged with each other;
the frame comprising a plurality of tube holes;
the tissue section tray comprising a plurality of tissue section cells;
the plurality of tube holes being separate from each other;
the plurality of tissue section cells being separate from each other;
a bottom of each of the plurality of tissue section cells being of ridge shaped;
a corresponding tube hole among the plurality of tube holes being aligned with a corresponding tissue section cell among the plurality of tissue section cells in response to the agitation platform being connected with the frame and the tissue section tray being connected with the agitation platform;
the specimen collector comprising a tubular body, a plunger button, a hollow shaft, a piston cylinder, a motor unit, a piston, a piston spring and a piston rod;
the hollow shaft and the piston cylinder being connected with each other;
the motor unit being configured to rotate the hollow shaft and the piston cylinder;
the motor unit being accommodated within the plunger button;
the motor unit contacting against the plunger button;
the piston being slidably inserted within the piston cylinder;
the piston spring being biased in between the piston cylinder and the motor unit;
the piston rod being connected in between the motor unit and the piston;
the specimen collector comprising a side window and a label;
the side window being formed on the tubular body;
the label being disposed on the plunger button;
the label being exposed via the side window;
the specimen collector comprising a pin;
the pin being connected with the piston rod;
the piston cylinder comprising an inner wall and a groove;
the groove being formed on the inner wall;
the pin being slidably inserted into the groove;
the specimen collector comprising a bearing;
the bearing being connected in between the hollow shaft and the piston cylinder;
the specimen collector comprising a hollow tip;
the hollow tip being connected with the hollow shaft; and
the hollow shaft being connected in between the piston cylinder and the hollow tip.

14. The dissection system as claimed in claim 13 comprising:
the airflow drying unit comprising a fan, an air duct and a plurality of air outlet slots;
the fan, the air duct and the plurality of air outlet slots being in fluid connection with one another;
a corresponding air outlet slot among the plurality of air outlet slots facing towards a corresponding tissue section cell among the plurality of tissue section cells in response to the agitation platform being connected with the frame and the tissue section tray being connected with the agitation platform;
the dissection platform comprising a switch unit;
the switch unit being disposed on the frame; and
the fan being electrically connected with the switch unit.

15. The dissection system as claimed in claim 13 comprising:
the waste collection unit comprising a vacuum flask and a vacuum pump; and
the vacuum flask and the vacuum pump being configured to be in fluid connection with one another.

16. The dissection system as claimed in claim 13 comprising:
the specimen collector comprising a filter;
the filter being accommodated within the hollow tip;
the hollow tip comprising an intermediate section, a flat end and a coating layer;
the intermediate section being of a conical shaped or a cylindrical shaped; and
the coating layer being coated on the flat end.

17. The dissection system as claimed in claim 13 comprising:
the specimen collector comprising a tip ejector;
the tip ejector being disposed on the tubular body and the hollow tip;
the tip ejector being configured to detach the hollow tip;
the tip ejector comprising an arm, a housing and an ejection spring;
the housing being fixed on the tubular body;
the arm being slidably disposed on the tubular body and the hollow tip;
the ejection spring being biased in between the arm and the housing.

18. The dissection system as claimed in claim 13 comprising:
the specimen collector comprising a tip ejector;
the tip ejector being disposed on the tubular body and the hollow tip;
the tip ejector being configured to detach the hollow tip;
the tip ejector comprising an arm, a housing and an ejection spring;
the housing being fixed on the tubular body;
the arm being slidably disposed on the tubular body and the hollow tip;
the ejection spring being biased in between the arm and the housing.

19. A dissection system comprising:
a dissection platform;
a specimen collector;
the dissection platform and the specimen collector being operatively associated with each other;
the dissection platform comprising a frame, an agitation platform, a tissue section tray, a solution dispenser unit, an airflow drying unit and a waste collection unit;
the agitation platform being movably connected with the frame;
the tissue section tray being removably connected with the agitation platform;
the solution dispenser unit being disposed on the frame;
the airflow drying unit being disposed on the frame;
the waste collection unit being disposed on the frame;
the agitation platform being maintained in a horizontal position with respect to the frame;
the agitation platform comprising an indent;
the tissue section tray comprising a block;
the tissue section tray being connected with the agitation platform by the indent and the block being engaged with each other;
the frame comprising a plurality of tube holes;
the tissue section tray comprising a plurality of tissue section cells;
the plurality of tube holes being separate from each other;

the plurality of tissue section cells being separate from each other;

a bottom of each of the plurality of tissue section cells being of ridge shaped;

a corresponding tube hole among the plurality of tube holes being aligned with a corresponding tissue section cell among the plurality of tissue section cells in response to the agitation platform being connected with the frame and the tissue section tray being connected with the agitation platform;

the airflow drying unit comprising a fan, an air duct and a plurality of air outlet slots;

the fan, the air duct and the plurality of air outlet slots being in fluid connection with one another;

a corresponding air outlet slot among the plurality of air outlet slots facing towards a corresponding tissue section cell among the plurality of tissue section cells in response to the agitation platform being connected with the frame and the tissue section tray being connected with the agitation platform;

the dissection platform comprising a switch unit;

the switch unit being disposed on the frame;

the fan being electrically connected with the switch unit;

the waste collection unit comprising a vacuum flask and a vacuum pump;

the vacuum flask and the vacuum pump being configured to be in fluid connection with one another;

the specimen collector comprising a tubular body, a plunger button, a hollow shaft, a piston cylinder, a motor unit, a piston, a piston spring and a piston rod;

the hollow shaft and the piston cylinder being connected with each other;

the motor unit being configured to rotate the hollow shaft and the piston cylinder;

the motor unit being accommodated within the plunger button;

the motor unit contacting against the plunger button;

the piston being slidably inserted within the piston cylinder;

the piston spring being biased in between the piston cylinder and the motor unit;

the piston rod being connected in between the motor unit and the piston;

the specimen collector comprising a side window and a label;

the side window being formed on the tubular body;

the label being disposed on the plunger button;

the label being exposed via the side window;

the specimen collector comprising a pin;

the pin being connected with the piston rod;

the piston cylinder comprising an inner wall and a groove;

the groove being formed on the inner wall;

the pin being slidably inserted into the groove;

the specimen collector comprising a bearing;

the bearing being connected in between the hollow shaft and the piston cylinder;

the specimen collector comprising a hollow tip;

the hollow tip being connected with the hollow shaft; and the hollow shaft being connected in between the piston cylinder and the hollow tip.

20. The dissection system as claimed in claim 19 comprising:

the specimen collector comprising a filter;

the filter being accommodated within the hollow tip;

the hollow tip comprising an intermediate section, a flat end and a coating layer;

the intermediate section being of a conical shaped or a cylindrical shaped; and the coating layer being coated on the flat end.

* * * * *